Sept. 1, 1959 A. L. DRUMMOND Plant Pat. 1,861

WALNUT TREE

Filed May 19, 1958

WITNESS

Addison E. Avery

INVENTOR

Arthur L. Drummond

Webster & Webster

ATTYS.

United States Patent Office

Plant Pat. 1,861
Patented Sept. 1, 1959

1,861

WALNUT TREE

Arthur L. Drummond, Pacific Grove, Calif.

Application May 19, 1958, Serial No. 736,417

1 Claim. (Cl. 47—62)

This discovery relates to a new and distinct variety of walnut tree; such variety having originated in my orchard near Gustine, California, as a seedling resultant from an open-pollenated cross between the Eureka as the seed parent and an unknown pollen parent.

More particularly, a nut which had fallen from a Eureka walnut tree sprouted; the seedling was permitted to grow to maturity under conditions of careful observation by me; and—upon bearing a crop—was recognized by me as being a variety having certain very distinct and desirable characteristics, as will hereinafter appear.

Subsequent to my discovery of the variety I asexually reproduced it by budding on root stock growing in my orchard located as aforesaid, and at maturity such reproductions of the variety were found to be true to the parent in all respects.

The present variety of walnut tree is characterized as to novelty and in comparison to the seed parent Eureka—which it most nearly resembles—by a larger nut with much softer shell; a higher percentage of sound, light colored kernels; and nuts which are much easier to harvest and among which are few "stick-tights."

In further comparison to the Eureka the present variety leaves out, and the catkins are in bloom, about two weeks later; the catkins occurring approximately three weeks subsequent to the Payne.

In addition, the tree of the instant variety is thrifty in growing habit, of good structure without splitting at the crotches, and a very productive bearer of commercially high grade nuts; the harvest being in the latter part of September, shortly after the Payne, but slightly earlier than the Eureka.

A further advantage of the variety resides in its resistance to sunburn; the trunk and branches—which are not brittle—evidencing no injury from sunlight, and also the nuts tend to grow in a shaded position on the branch; i.e., in the shelter of the leaves, and are thus effectively protected. The variety is therefore especially adapted for growing in an area having a hot summer climate, as in the Central Valley of California.

Figure 2:
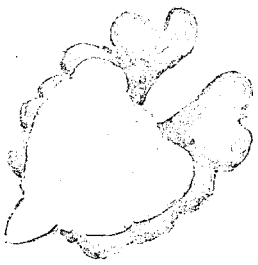
Fig. 2 is an elevation of a kernel half taken from the inner side, and with sufficient skin removed to expose the meat.
Figure 1:
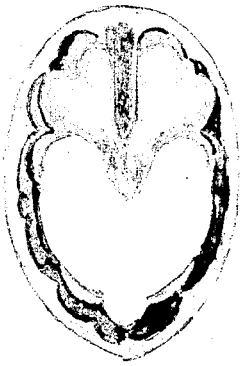
Fig. 1 is an elevation of one-half of a shell, with the corresponding portion of the kernel remaining therein.
Figure 3:
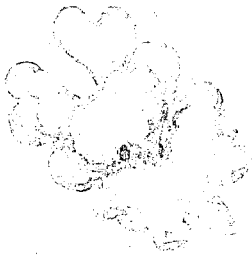
Fig. 3 is an elevation of a kernel half taken from the outer side.

Referring now more specifically to the botanical details of this new and distinct variety of walnut tree, the following is an outline description thereof; all major color plate identifications being by reference to Maerz and Paul Dictionary of Color:

Tree growth characteristics:

*Size at maturity.*—Medium.
*Vigor.*—Medium.
*Habit of growth.*—Medium.

*Foliage.*—Medium dense. Size of leaves—large. Color of leaves: top side—medium green (22–L–7); under side—lighter green (21–L–6).
*Color of bark.*—Medium.
*Time of leafing (date when tip buds average one inch in length).*—Late.

Flowering habits:

*Age at which tree starts producing catkins.*—Early.
*Number of catkins produced.*—Abundant.
*Size of catkins.*—Large.
*Time of pollen shedding.*—Late.
*Age at which tree starts producing pistillate flowers.*—Early.
*Number of pistillate flowers produced by young trees.*—Abundant.
*Percentage of lateral buds on long twigs of the previous season's growth that produce current season's shoots bearing pistillate flowers.*—1958, 65%.
*Number of pistillate flowers per inflorescence (average of twenty flowering tips).*—1958, average number 1.6.
*Number of pistillate flowers produced by mature trees.*—Abundant.
*Number of pistillate flowers per inflorescence (average of twenty).*—1958, average number 1.9.
*Time when pistillate flowers are receptive.*—Late.
*Date of peak receptivity.*—April 25, 1958.
*Coincidence of staminate and pistillate bloom.*—Good coincidence of pollen shedding and pistillate receptivity.

Productivity: Productive; yields heavily.

Maturity: Medium ripening period.

Evenness of maturity: Period between time first and last nuts are ready to harvest—short.

Nut characteristics:

*Size (average of ten nuts picked as apparently representative size), 1957.*—Length—45.9 millimeters. Diameter at suture—32.7 millimeters. Diameter cheek to cheek—34.4 millimeters.
*Weight (average of ten nuts picked as apparently representative weight), 1957.*—Average weight of ten nuts—156.1 grams. Average weight of ten kernels—74.0 grams. Percent kernel—47.4.
*Uniformity of size.*—Little variation.
*Shape.*—Long cylindrical. Blossom end—rounded; symmetrical. Basal end—rounded.
*Color of shell.*—Light tan (12–C–7).
*Thickness of shell.*—Medium thick.
*Seal.*—Fair to good.
*Roughness of shell.*—Medium.
*Fill.*—Good.
*Plumpness of Kernel.*—Plump.
*Kernel shrivel.*—None.
*Kernel color.*—High percentage of kernels light straw or golden (10–H–5 to 13–K–8); few amber color.
*Speckling of kernels.*—No speckling in the majority; few lightly speckled.
*Veining of kernels.*—No veining in the majority; few lightly veined.
*Flesh color.*—Ivory cast (9–C–2 to 10–B–2).
*Flavor.*—Good.

The mentioned previously existing varieties of walnuts are unpatented.

The tree and its nuts herein described may vary in slight detail due to climatic and soil conditions under which the variety may be grown.

Having thus described my invention, I claim:

A new and distinct variety of walnut tree, as illustrated and described, characterized by thrifty growing habit, good structure, bark which does not tend to sunburn, productive bearing of large nuts which tend to grow in the shelter of the foliage, and a harvest which occurs in the latter part of September shortly after the Payne and slightly earlier than the Eureka; and further characterized—in comparison to said Eureka—by leafing out and bearing catkins later, and by nuts which are easier to harvest and with few "stick-tights," larger with a softer shell, and a higher percentage of sound, light-colored kernels.

No references cited.